US00PP26929P2

(12) United States Plant Patent
Wood

(10) Patent No.: US PP26,929 P2
(45) Date of Patent: Jul. 12, 2016

(54) ***HYDRANGEA* PLANT NAMED 'SMNHMSIGMA'**

(50) Latin Name: *Hydrangea macrophylla*
Varietal Denomination: SMNHMSIGMA

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/544,628

(22) Filed: Jan. 23, 2015

(51) Int. Cl.
*A01H 5/02* (2006.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Hydrangea* plant named 'SMNHMSIGMA', characterized by its compact, upright, outwardly spreading and mounding plant habit; strong and sturdy stems; remontant flowering habit; dark green-colored leaves; mophead-type inflorescences with intense deep pink-colored sterile flowers that can easily be "blued" with aluminum sulfate treatments; and good garden performance.

2 Drawing Sheets

Botanical designation: *Hydrangea macrophylla.*
Cultivar denomination: 'SMNHMSIGMA'.

BACKGROUND OF THE INVENTION

The present invention relates to a new and distinct *Hydrangea* plant, botanically known as *Hydrangea macrophylla* and hereinafter referred to by the name 'SMNHMSIGMA'.

The new *Hydrangea* plant is a product of a planned breeding program conducted by the Inventor in Grand Haven, Mich. The objective of the breeding program was to develop new compact and reblooming *Hydrangea* plants with strong stems and attractive inflorescences.

The new *Hydrangea* plant originated from an open-pollination in July, 2008 of *Hydrangea macrophylla* 'Robert', disclosed in U.S. Plant Pat. No. 20,020, as the female, or seed parent and an unknown selection of *Hydrangea macrophylla*, as the male, or pollen, parent. The new *Hydrangea* plant was discovered and selected by the Inventor as a single flowering plant from within the progeny of the stated open-pollination in a controlled environment in Grand Haven, Mich. in June, 2011.

Asexual reproduction of the new *Hydrangea* plant by softwood cuttings in a controlled environment in Grand Haven, Mich. since June, 2011 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNHMSIGMA'. These characteristics in combination distinguish 'SMNHMSIGMA' as a new and distinct *Hydrangea* plant:

1. Compact, upright, outwardly spreading and mounding plant habit.
2. Strong and sturdy stems.
3. Remontant flowering habit.
4. Dark green-colored leaves.
5. Mophead-type inflorescences with intense dark pink-colored sterile flowers that can easily be "blued" with aluminum sulfate treatments.
6. Good garden performance.

Plants of the new *Hydrangea* differ from plants of the female parent, 'Robert', in the following characteristics:

1. Plants of the new *Hydrangea* have stronger stems than plants of 'Robert'.
2. Sterile flower sepals of plants of the new *Hydrangea* are richer and more intense in color than sterile flower sepals of plants of 'Robert'.
3. Plants of the new *Hydrangea* are more easily "blued" with aluminum sulfate than plants of 'Robert'.
4. Plants of the new *Hydrangea* have a stronger reblooming habit than plants of 'Robert'.

Plants of the new *Hydrangea* can be compared to plants of *Hydrangea macrophylla* 'Nikko Blue', not patented. In side-by-side comparisons, plants of the new *Hydrangea* differed primarily from plants of 'Nikko Blue' in the following characteristics:

1. Sterile flower sepals of plants of the new *Hydrangea* were darker and more intense in color than sterile flower sepals of plants of 'Nikko Blue'.
2. Plants of the new *Hydrangea* had a stronger reblooming habit than plants of 'Nikko Blue'.

Plants of the new *Hydrangea* can also be compared to plants of *Hydrangea macrophylla* 'Berner', disclosed in U.S. Plant Pat. No. 22,329. In side-by-side comparisons, plants of the new *Hydrangea* differed primarily from plants of 'Berner' in the following characteristics:

1. Sterile flower sepals of plants of the new *Hydrangea* were smaller and richer and more intense in color than sterile flower sepals of plants of 'Berner'.
2. Plants of the new *Hydrangea* had a stronger reblooming habit than plants of 'Berner'.
3. Plants of the new *Hydrangea* were more easily "blued" with aluminum sulfate than plants of 'Berner'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SMNHMSIGMA' grown in an outdoor nursery.

The photograph on the second sheet is a close-up view of typical inflorescences of 'SMNHMSIGMA'; the inflorescence on the left is from a plant that was not treated with aluminum sulfate and the inflorescence on the right is from a plant that was treated with aluminum sulfate.

DETAILED BOTANICAL DESCRIPTION

Plants used for the aforementioned photographs and the following description were grown during the summer in three-gallon containers in a polypropylene-covered shadehouse in Grand Haven, Mich. and under cultural practices typical of commercial *Hydrangea* production. During the production of the plants, day temperatures ranged from 18° C. to 27° C. and night temperatures ranged from 5° C. to 10° C. Plants of the new *Hydrangea* were two years old when the photographs and description were taken. Plants were overwintered in a polyethylene-covered greenhouse. Some plants were treated with aluminum sulfate to "blue" the flowers. During the production of the plants, the soil pH ranged from 5.0 to 6.0. In the following description, color references are made to The Royal Horticultural Society Colour Chart, 1995 Edition, except where general terms of ordinary dictionary significance are used.

Botanical description: *Hydrangea macrophylla* 'SMNHMSIGMA'.

Parentage:

*Female, or seed, parent.*—*Hydrangea macrophylla* 'Robert', disclosed in U.S. Plant Pat. No. 20,020.

*Male, or pollen, parent.*—Unknown selection of *Hydrangea macrophylla*, not patented.

Propagation:

*Type cutting.*—By softwood cuttings.

*Time to initiate roots, summer.*—About 18 days at temperatures about 27° C.

*Time to produce a rooted young plant, summer.*—About 60 days at temperatures about 27° C.

*Root description.*—Fine to thick; fibrous; white and brown in color.

*Rooting habit.*—Freely branching; dense.

Plant description:

*Plant form and growth habit.*—Perennial deciduous shrub; compact, upright, outwardly spreading and mounding plant habit; strong and sturdy lateral branches; freely branching habit with about 36 lateral branches developing per plant; vigorous growth habit.

*Plant height.*—About 66 cm.

*Plant diameter or area of spread.*—About 82 cm.

*Lateral branches.*—Length: About 34 cm. Diameter: About 7 mm. Internode length: About 6 cm. Texture: Smooth, glabrous. Strength: Strong, sturdy. Aspect: Erect to about 45° from vertical. Color: Close to 145B.

Leaf description:

*Arrangement.*—Opposite, simple.

*Length.*—About 16.5 cm.

*Width.*—About 8 cm to 11 cm.

*Shape.*—Ovate.

*Apex.*—Acute to acuminate.

*Base.*—Cuneate.

*Margin.*—Serrate.

*Texture, upper and lower surfaces.*—Smooth, glabrous; leathery.

*Venation pattern.*—Pinnate.

*Color.*—Developing leaves, upper surface: Close to 137A. Developing leaves, lower surface: Close to 137C. Fully expanded leaves, upper surface: Close to 139A; venation, close to 138A. Fully expanded leaves, lower surface: Close to 137C; venation, close to 137C and 59A.

*Petioles.*—Length: About 3.5 cm. Diameter: About 4 mm. Texture, upper and lower surfaces: Smooth, glabrous. Color, upper surface: Close to 137C. Color, lower surface: Close to 137C and 59A.

Flower description:

*Flower type and habit.*—Single sterile and fertile flowers arranged on terminal mophead cymes that are roughly hemispherical in shape; flowers face upright to outwardly.

*Fragrance.*—None detected.

*Natural flowering season.*—Plants flower throughout the summer in Grand Haven, Mich.; flowering remontant; flowers not persistent.

*Quantity of flowers.*—Freely flowering habit; about 91 fertile flowers and about 306 sterile flowers developing per inflorescence.

*Inflorescence height.*—About 13 cm.

*Inflorescence diameter.*—About 19 cm.

*Flower diameter, fertile flowers.*—About 2.6 mm.

*Flower depth (height), fertile flowers.*—About 2.2 mm.

*Flower diameter, sterile flowers.*—About 3 cm to 4 cm.

*Flower depth (height), sterile flowers.*—About 2.5 cm.

*Flower buds, fertile and sterile flowers.*—Length: About 3 mm. Diameter: About 3 mm. Shape: Obovate. Color, not treated with aluminum sulfate: Close to 145B and 73C. Color, treated with aluminum sulfate: Close to 145B and 104D.

*Petals, fertile flowers.*—Quantity and arrangement: About five in a single whorl. Length: About 2 mm. Width: About 1.2 mm. Shape: Ovate. Apex: Acute. Base: Cuneate. Margin: Entire. Texture, upper and lower surfaces: Smooth, glabrous. Color: When opening, upper surface: Close to 145D; towards the margins, close to 145B; towards the apex, close to 63A. When opening, lower surface: Blending from base towards the apex and margins, close to 145D, 145C, 145B and 145A. Fully opened, upper surface: Close to 145D; towards the margins, close to 145B; towards the apex, close to 63A; color does not change with development. Fully opened, lower surface: Blending from base towards the center, close to 145D and 145C; towards the apex, close to 63D; occasional spot, close to 145A; color does not change with development.

*Petals, sterile flowers*.—Quantity and arrangement: About four in a single whorl. Length: About 2 mm. Width: About 1 mm. Shape: Ovate. Apex: Acute. Base: Cuneate. Margin: Entire. Texture, upper and lower surfaces: Smooth, glabrous. Color, plants not treated with aluminum sulfate: When opening, upper and lower surfaces: Close to 73C. Fully opened, upper surface: Close to 73C; with development, inner stripes (venation) becoming closer to 64D and 63D. Fully opened, lower surface: Close to 73C; with development, inner stripes (venation) becoming closer to 62D and 73B. Color, plants treated with aluminum sulfate: When opening, upper and lower surfaces: Close to 104D. Fully opened, upper and lower surfaces: Close to 104D; color does not change with development.

*Sepals, sterile flowers only*.—Quantity and arrangement: About four in a single whorl. Length: About 2 cm. Width: About 2.2 cm. Shape: Ovate. Apex: Acute. Base: Obtuse. Margin: Entire. Texture, upper and lower surfaces: Smooth, glabrous. Color, plants not treated with aluminum sulfate: When opening, upper surface: Close to 68A; towards the base, close to 145B. When opening, lower surface: Close to 68C. Fully opened, upper surface: Close to 68A; with development, inner stripes (venation) becoming closer to 64D and 63D. Fully opened, lower surface: Close to 68C; with development, inner stripes (venation) becoming closer to 62D and 73B. Color, plants treated with aluminum sulfate: When opening, upper surface: Close to 93B. When opening, lower surface: Close to 93D. Fully opened, upper surface: Close to 93B; color does not change with development. Fully opened, lower surface: Close to 93C; color does not change with development.

*Pedicels, fertile flowers*.—Length: About 3 mm. Diameter: About 1 mm. Angle: About 15° to 35° from inflorescence axis. Strength: Strong, sturdy. Texture: Smooth, glabrous. Color: Close to 145B.

*Pedicels, sterile flowers*.—Length: About 1.5 cm. Diameter: About 1 mm. Angle: About 45° from inflorescence axis. Strength: Strong, sturdy. Texture: Smooth, glabrous. Color, plants not treated with aluminum sulfate: Close to 145B and 68A. Color, plants treated with aluminum sulfate: Close to 145B and 93C.

*Reproductive organs, fertile flowers*.—Stamens: Quantity per flower: About eight to ten. Filament length: About 1.2 mm. Filament color: Close to 145D. Anther shape: Round. Anther length: About 0.25 mm. Anther color: Close to 145D. Pollen amount: Scarce. Pollen color: Close to 155B. Pistils: Pistil quantity per flower: One, two to three-lobed. Pistil length: About 0.7 mm. Stigma shape: Oblong. Stigma color: Close to 155B and 145D. Style length: About 0.5 mm. Style color: Close to 155B and 145D. Ovary color: Close to 155B and 145B.

*Reproductive organs, sterile flowers*.—Stamens: Quantity per flower: If present, about six to eight. Filament length: About 1.2 mm. Filament color: Close to 145D. Anther shape: Round. Anther length: About 0.25 mm. Anther color: Close to 145D. Pollen amount: Scarce. Pollen color: Close to 155B. Pistils: Pistil quantity per flower: One, two to three-lobed. Pistil length: About 0.7 mm. Stigma shape: Oblong. Stigma color: Close to 155B and 145D. Style length: About 0.5 mm. Style color: Close to 155B and 145D. Ovary color: Close to 155B and 145B.

*Seeds, observed on fertile flowers only*.—Quantity per inflorescence: Numerous. Size: Less than 0.1 mm by less than 0.1 mm; dust-like. Color: Brown.

Disease & pest resistance: Plants of the new *Hydrangea* have been observed to be resistant to Mildew. Plants of the new *Hydrangea* have not been observed to be resistant to pests and other pathogens common to *Hydrangea* plants.

Garden performance: Plants of the new *Hydrangea* have been shown to exhibit good garden performance. Plants of the new *Hydrangea* have been observed to tolerate temperatures ranging from −30° C. to 36° C.

It is claimed:

1. A new and distinct *Hydrangea* plant named 'SMNHM-SIGMA' as illustrated and described.

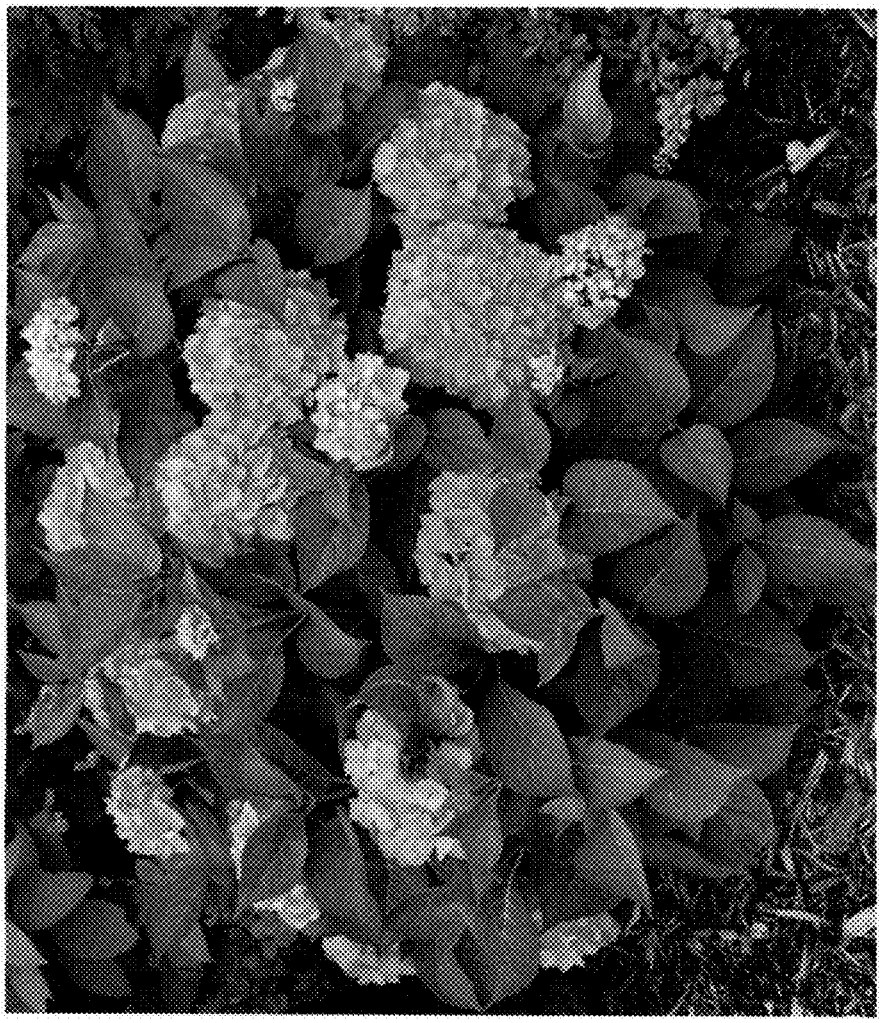

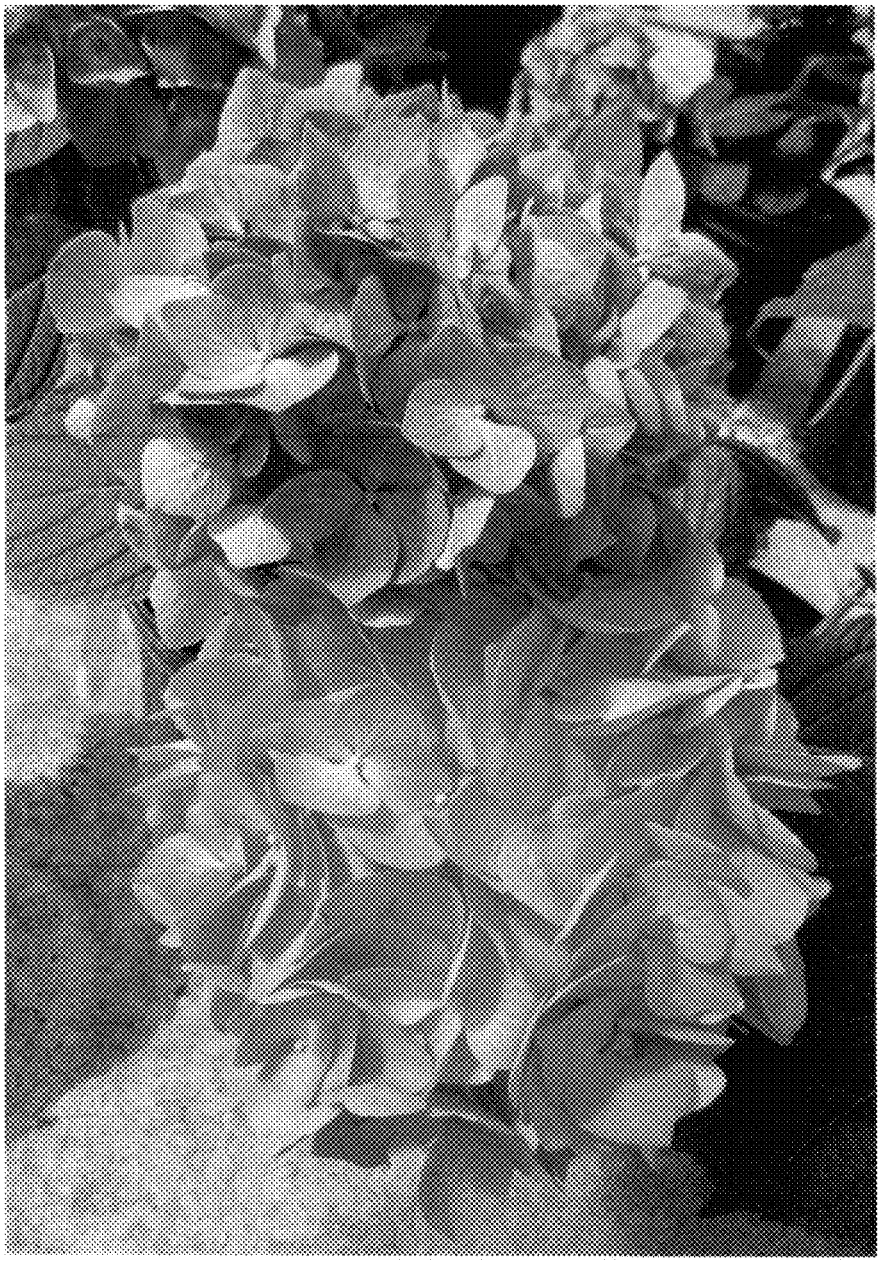

* * * * *